(12) United States Patent
Hewitt

(10) Patent No.: US 6,608,220 B1
(45) Date of Patent: Aug. 19, 2003

(54) CONVERSION OF BISNORALCOHOL TO BISNORALDEHYDE

(75) Inventor: Bradley D. Hewitt, Kalamazoo, MI (US)

(73) Assignee: Pharmacia & Upjohn Company, Kalamazoo, MI (US)

(*) Notice: Subject to any disclaimer, the term of this patent is extended or adjusted under 35 U.S.C. 154(b) by 0 days.

(21) Appl. No.: 08/809,719

(22) PCT Filed: Oct. 27, 1994

(86) PCT No.: PCT/US94/12196

§ 371 (c)(1),
(2), (4) Date: Mar. 18, 1997

(87) PCT Pub. No.: WO95/16698

PCT Pub. Date: Jun. 22, 1995

(51) Int. Cl.$^7$ .................................................. C07J 9/00
(52) U.S. Cl. ..................................................... 552/555
(58) Field of Search ......................................... 552/555

(56) References Cited

U.S. PATENT DOCUMENTS

| | | | |
|---|---|---|---|
| 4,985,546 A | * 1/1991 | Miley et al. | 534/729 |
| 5,136,102 A | 8/1992 | Fried | 568/402 |
| 5,155,278 A | 10/1992 | Fried | 568/471 |
| 5,155,279 A | 10/1992 | Fried | 568/471 |
| 5,155,280 A | 10/1992 | Fried | 568/471 |
| 5,334,665 A | * 8/1994 | Lawson et al. | 525/289 |
| 5,710,293 A | * 1/1998 | Li | 552/595 |
| 5,856,604 A | * 1/1999 | Stine et al. | 585/310 |
| 5,856,607 A | * 1/1999 | Kim | 585/448 |

FOREIGN PATENT DOCUMENTS

| | | | |
|---|---|---|---|
| DE | 42 36 887 | 5/1994 | 47/23 |
| JP | J5 615498 | 11/1981 | |
| JP | 56152498 | * 11/1981 | |

OTHER PUBLICATIONS

Anelli et al., "Fast and selective oxidation of primary alcohols to aldehydes or to carboxylic acids and of secondary alcohols to ketones mediated by oxoammonium salts under two–phase conditions", J. Org. Chem., vol. 52, 2559–2562, 1987.*
Semmelhack et al., "Oxidation of alcohols to aldehydes with oxygen and cupric ion, mediated by nitrosonium ion". J. Am. Chem. Soc., vol. 106, 3374–3376, 1984.*
CA 122:9868.
Nitta, I., et al., *Chem. Soc. Jap.*, 58, pp. 1081–1082 (1985).
Synthesis, pp. 190–202 (1971).
Synthesis, pp. 401–414 (1971).
J. Org. Chem., 52, 2559 (1987).
J. Org. Chem., 56, 6110 (1991).
J. Am. Chem., Soc., 106, 3374 (1984).

* cited by examiner

*Primary Examiner*—Barbara P. Badio
(74) *Attorney, Agent, or Firm*—James D. Darnley, Jr.; Bruce Stein; John H. Engelmann

(57) ABSTRACT

The present invention is a process for the conversion of bisnoralcohol to bisnoraldehyde (II), which is a known intermediate in the synthesis of progesterone.

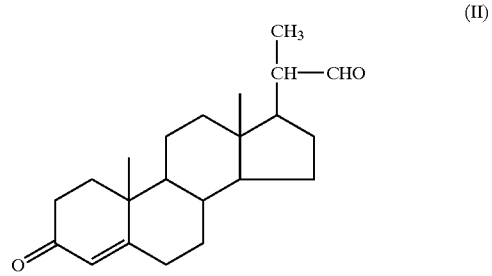

18 Claims, No Drawings

CONVERSION OF BISNORALCOHOL TO BISNORALDEHYDE

This application is a 371 of PCT/US94/12196 filed Oct. 27, 1994.

BACKGROUND OF THE INVENTION

1. Field of the Invention

The present invention is a process for the conversion of bisnoralcohol (I) to bisnoraldehyde (II) which is a known intermediate in the synthesis of progesterone.

2. Description of the Related Art

The oxidation of bisnoralcohol (I) to bisnoraldehyde (II) is a well known process.

4-hydroxy-TEMPO (4-hydroxy-2,2,6,6-tetramethylpiperidine-1-oxyl) is known, see Synthesis, 190–202 and 401–414 (1971).

J. Org. Chem., 52, 2559 (1987) discloses TEMPO and 4-Methoxy-TEMPO catalyzed, two-phase oxidation of primary alcohols and secondary alcohols to aldehydes and ketones, respectively, using potassium bromide and 0.35 M sodium hypochlorite buffered to Ph 8.5 with sodium bicarbonate.

J. Org. Chem., 56, 6110 (1991) discloses the use of stoichiometric amounts of oxammonium salts, generated by treatment of TEMPO or 4-acetylamino-TEMPO with organic sulfonic acids, for the selective oxidation of primary or secondary alcohols to aldehydes or ketones, respectively.

J. Am. Chem. Soc., 106, 3374 (1984) discloses the use of TEMPO or 4-hydroxy-TEMPO to catalyze the oxidation of primary or secondary alcohols to aldehydes or ketones, respectively, by oxygen and copper (II) salts.

U.S. Pat. No. 5,136,102 discloses the use of TEMPO or 4-substituted TEMPO derivatives and a bromide containing salt to catalyze the oxidation of secondary alcohols to ketones with nitric acid and oxygen.

U.S. Pat. No. 5,155,278 discloses the use of TEMPO or 4-substituted TEMPO derivatives to catalyze the oxidation of primary alcohols to aldehydes with nitric acid and oxygen.

U.S. Pat. No. 5,155,279 discloses the use of TEMPO or 4-substituted TEMPO derivatives to catalyze the selective oxidation of primary alcohols to aldehydes with nitric acid in the absence of oxygen.

U.S. Pat. No. 5,155,280 discloses the use of TEMPO or 4-substituted TEMPO derivatives and an alkali metal nitrosodisulfonate salt to catalyze the selective oxidation of primary alcohols to aldehydes with oxygen in the absence of nitric acid.

Japanese patent J5 6152498 discloses the oxidation of bisnoralcohol to bisnoraldehyde using dimethyl sulfide and N-chlorosuccinimde or chlorine.

SUMMARY OF INVENTION

Disclosed is a process for the production bisnoraldehyde (II)

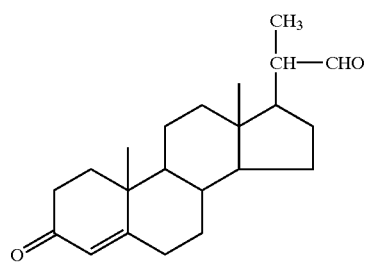

which comprises:
(1) forming a mixture of
  (a) bisnoralcohol (I)

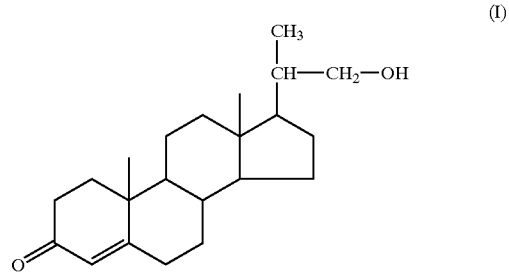

(b) a catalytic amount of 4-hydroxy-2,2,6,6-tetramethylpiperidine-1-oxyl in a pH range of about 8.5 to about 10.5 in a temperature range of about −10° to about 15°, and
(2) contacting the mixture of step (1) with a stoichiometric amount of hypochlorite.

DETAILED DESCRIPTION OF THE INVENTION

Bisnoraldehyde (II) is known to be useful as an intermediate in the synthesis of progesterone and hydrocortisone, see J. Am. Chem. Soc., 74, 5933 (1952).

The present invention is practiced by (1) forming a mixture of bisnoralcohol (I), a catalytic amount of 4-hydroxy TEMPO in a pH range of about 8.5 to about 10.5 and in a temperature range of about −10° to about 15°, and (2) contacting the mixture of step (1) with a stoichiometric amount of hypochlorite. It is preferred to perform the reaction in the presence of bromide, preferably a catalytic amount of the bromide. The mixture can be cooled at any point prior to the addition of the hypochlorite.

Operable amounts of the 4-hydroxy-TEMPO are from about 0.025 mole percent to about 15 mole percent; it is preferred that the amount of the 4-hydroxy-TEMPO be from about 0.025 mole percent to about 2.5 mole percent. Operable amounts of the bromide are from about 5 mole percent to about 25 mole percent; it is preferred that the amount of bromide be from about 10 mole percent to about 15 mole percent. The pH is preferably regulated by the use of bicarbonate. Operable amounts of bicarbonate are from about 5 mole percent to about 30 mole percent; it is preferred that the amount of bicarbonate be from about 10 mole percent to about 20 mole percent. The cation of the bromide or bicarbonate is not important as long as it is soluble; preferred cation are sodium, potassium and lithium, more preferably sodium or potassium. Operable solvents include dichloroethane, toluene, ethyl acetate, methyl tert-butyl ether, dichloromethane, o-dichlorobenzene chlorobenzene and chloroform; it is preferred that the solvent be methylene chloride. While the operable solvents are organic water immiscible solvents, a small amount of water is operable and even preferred as is known to those skilled in the art. In addition, the hypochlorite is added as an aqueous mixture. It is preferred that the reaction temperature be in the range of about −5° to about 5°. It is preferred that the hypochlorite is added over a period of from about 1 hr to about 6 hr. It is preferred that the amount of hypochlorite be from about 95 mole percent to about 120 mole percent. Following step (2) it is preferred to quench the reaction mixture. Operable quenching agents include bisulfite, thiosulfate, dimethylsulfide, trimethylphosphate and triethylphosphate; it is preferred that the quenching agent be sodium or potassium thiosulfate.

The process of the present invention can be practiced in either batch mode or continuous mode as is known to those skilled in the art.

The reaction mixture is worked up by methods well known to those skilled in the art.

The bisnoraldehyde (II) can be transformed to progesterone by known methods, see *J. C. S. Chem. Comm.*, 314 (1969) and *Tet. Lett.*, 985 (1969).

Definitions and Conventions

The definitions and explanations below are for the terms as used throughout this entire document including both the specification and the claims.

Definitions

All temperatures are in degrees Centigrade.

4-hydroxy-TEMPO refers to 4-hydroxy-2,2,6,6-tetramethylpiperidine-1-oxyl.

TEMPO refers to 2,2,6,6-tetramethylpiperidine-1-oxyl.

EXAMPLES

Without further elaboration, it is believed that one skilled in the art can, using the preceding description, practice the present invention to its fullest extent.

The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

Bisnoralcohol (I) to Bisnoraldehyde (II) at 1° with 4-Hydroxy-TEMPO

A mixture of bisnoralcohol (I, 4 g), 4-hydroxy-2,2,6,6-tetramethylpiperidine-1-oxyl (4-hydroxy-TEMPO, 10 mg), potassium bromide (133 mg), sodium bicarbonate (133 mg), dichloromethane (14 ml) and water (2.2 ml) are cooled to 1°. While maintaining this temperature, aqueous sodium hypochlorite (14%, 6.3 ml) is added over a five hr period. The reaction is complete and aqueous sodium thiosulfate is added, the two phases were separated, and the bisnoraldehyde product is crystallized by replacing the dichloromethane with heptane to give the title compound, mp=153–154°; NMR (CDCl$_3$) 9.56, 5.73, 2.2–2.5, 1.2–2.1, 1.20, 1.10, 0.79 δ; $[\alpha]_D^{22}$=+83.4° (methylene chloride, c=1).

Example 2

Bisnoralcohol (I) to Bisnoraldehyde (II) at 10° with 4-Hydroxy-TEMPO

Following the general procedure of EXAMPLE 1 and making non-critical variations the process of EXAMPLE 1 is repeated at 10° and the title compound is obtained.

Example 3

Bisnoralcohol (I) to Bisnoraldehyde (II) at −10° with 4-Hydroxy-TEMPO

Following the general procedure of EXAMPLE 1 and making non-critical variations the process of EXAMPLE 1 is repeated at −10° and the title compound is obtained.

Example 4

Bisnoralcohol (I) to Bisnoraldehyde (II) at 1° with 4-Hydroxy-TEMPO

Following the general procedure of EXAMPLE 1 and making non-critical variations the process of EXAMPLE 1 is repeated using 500 mg of 4-hydroxy-TEMPO and the title compound is obtained.

Example 5

Bisnoralcohol (I) to Bisnoraldehyde (II) at 1° with 4-Hydroxy-TEMPO

Following the general procedure of EXAMPLE 1 and making non-critical variations the process of EXAMPLE 1 is repeated using 5 mg of 4-hydroxy-TEMPO and the title compound is obtained.

Example 6

Bisnoralcohol (I) to Bisnoraldehyde (II) with 4-oxo-TEMPO

A mixture of bisnoralcohol (I, 6.6 g), 4-oxo-2,2,6,6-tetramethylpiperidine-1-oxyl (18 mg), dichloromethane (30 ml), sodium bicarbonate (180 mg), potassium bromide (238 mg) and water (5 ml) is cooled to 1°. Then aqueous sodium hypochlorite (14.6%, 11.4 ml) is added to the mixture over a 15 min period. The reaction produced the title compound but in only a 7% conversion of bisnoralcohol with 58% selectivity for bisnoraldehyde.

CHART A

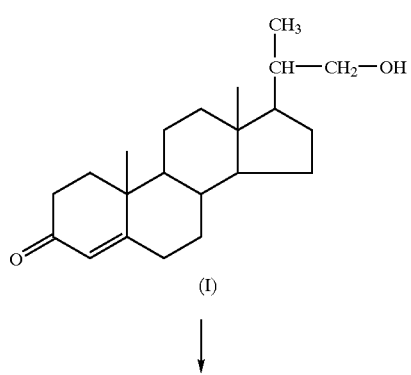

-continued

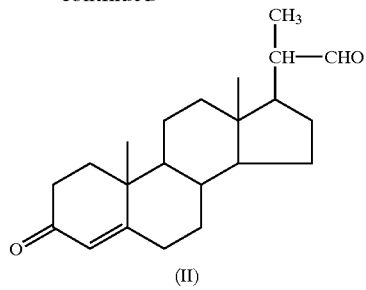

(II)

What is claimed is:
1. A process for the production bisnoraldehyde (II)

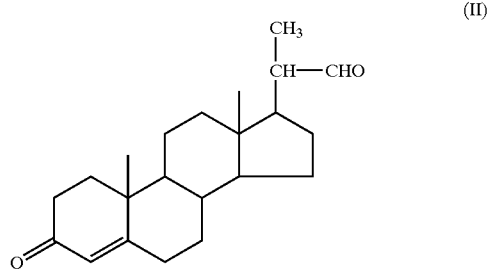

which comprises:
(1) forming a mixture of
   (a) bisnoralcohol (I)

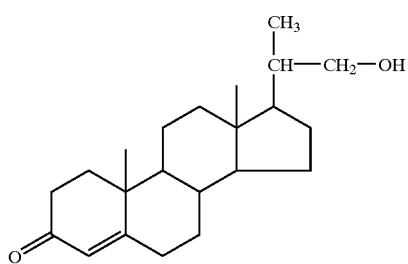

(b) a catalytic amount of 4hydroxy-2,2,6,6-tetramethylpiperidine-1-oxyl in a pH range of about 8.5 to about 10.5 in a temperature range of about −10° to about 15°, and
(2) contacting the mixture of step (1) with a stoichiometric amount of hypochlorite in the presence of a catalytic amount of bromide.

2. A process for the production of bisnoraldehyde (II) according to claim 1 where the catalytic amount of the 4hydroxy-2,2,6,6-tetramethylpiperidine-1-oxyl is from about 0.025 mole percent to about 15 mole percent.

3. A process for the production of bisnoraldehyde (II) according to claim 2 where the catalytic amount of the 4hydroxy-2,2,6,6-tetramethylpiperidine-1-oxyl is from about 0.025 mole percent to about 2.5 mole percent.

4. A process for the production of bisnoraldehyde (II) according to claim 1 where the catalytic amount of bromide is from about 5 mole percent to about 25 mole percent.

5. A process for the production of bisnoraldehyde (II) according to claim 4 where the catalytic amount of bromide is from about 10 mole percent to about 15 mole percent.

6. A process for the production of bisnoraldehyde (II) according to claim 1 where the pH is regulated by the presence of bicarbonate.

7. A process for the production of bisnoraldehyde (II) according to claim 6 where the amount of bicarbonate is from about 5 mole percent to about 30 mole percent.

8. A process for the production of bisnoraldehyde (II) according to claim 7 where the amount of bicarbonate is from about 10 mole percent to about 20 mole percent.

9. A process for the production of bisnoraldehyde (II) according to claim 1 which is performed in the presence of a solvent selected from the group consisting of dichloroethane, toluene, ethyl acetate, methyl tert-butyl ether, dichloromethane, o-dichlorobenzene chlorobenzene and chloroform.

10. A process for the production of bisnoraldehyde (II) according to claim 9 where the solvent is methylene chloride.

11. A process for the production of bisnoraldehyde (II) according to claim 1 where the temperature is range is from about −5 to about 5°.

12. A process for the production of bisnoraldehyde (II) according to claim 1 where amount of hypochlorite is from about 95 mole percent to about 120 mole percent.

13. A process for the production of bisnoraldehyde (II) according to claim 1 where the bisnoralcohol (I), the catalytic amount of 4-hydroxy-2,2,6,6-tetramethylpiperidine-1-oxyl, the catalytic amount of bromide and bicarbonate are all mixed together prior to cooling to about −10° to about 15°.

14. A process for the production of bisnoraldehyde (II) according to claim 1 where the reaction mixture of step (2) is quenched.

15. A process for the production of bisnoraldehyde (II) according to claim 14 where the reaction mixture of step (2) is quenched with a quenching agent selected from the group consisting of bisulfite, thiosulfate, dimethylsulfide, trimethylphosphate and triethylphosphate.

16. A process for the production of bisnoraldehyde (II) according to claim 15 where the quenching agent is sodium or potassium thiosulfate.

17. A process for the production of bisnoraldehyde (II) according to claim 1 which is performed in a non-continuous or batch method.

18. A process for the production of bisnoraldehyde (II) according to claim 1 which is performed in a continuous method.

* * * * *